United States Patent
Tsukashima et al.

(10) Patent No.: US 11,529,168 B2
(45) Date of Patent: Dec. 20, 2022

(54) CANNULA WITH ILLUMINATION

(71) Applicant: Rebound Therapeutics Corporation, Irvine, CA (US)

(72) Inventors: Ross Tsukashima, Irvine, CA (US); Donald Joseph Fuller, Irvine, CA (US); Jack H. Schmidt, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 146 days.

(21) Appl. No.: 16/550,162

(22) Filed: Aug. 23, 2019

(65) Prior Publication Data
US 2021/0052299 A1 Feb. 25, 2021

(51) Int. Cl.
| A61B 17/34 | (2006.01) |
| A61B 1/04 | (2006.01) |
| A61B 1/313 | (2006.01) |
| A61B 1/00 | (2006.01) |
| A61B 1/06 | (2006.01) |
| A61B 90/30 | (2016.01) |
| A61B 5/00 | (2006.01) |

(52) U.S. Cl.
CPC ...... *A61B 17/3423* (2013.01); *A61B 1/00096* (2013.01); *A61B 1/042* (2013.01); *A61B 1/0669* (2013.01); *A61B 1/313* (2013.01); *A61B 5/0042* (2013.01); *A61B 90/30* (2016.02)

(58) Field of Classification Search
CPC . A61B 17/3423; A61B 1/313; A61B 17/2018; A61B 17/0231; A61B 17/3421; A61B 90/361; A61B 1/0669; A61B 1/07; A61B 1/042
See application file for complete search history.

(56) References Cited

U.S. PATENT DOCUMENTS

| 5,036,834 A * | 8/1991 | Sugiyama | A61B 1/00096 385/119 |
| 5,957,832 A * | 9/1999 | Taylor | A61B 1/00193 600/172 |
| 7,087,014 B2 | 8/2006 | Sasaki | |
| 10,105,042 B2 * | 10/2018 | Davis | A61B 17/3423 |
| 2005/0191046 A1 * | 9/2005 | Dehmel | A61B 1/00126 396/17 |
| 2006/0069314 A1 | 3/2006 | Farr | |

(Continued)

FOREIGN PATENT DOCUMENTS

| DE | 9414957 | 9/1995 |
| JP | 2003509096 | 3/2003 |
| KR | 1020170132254 | 12/2017 |

OTHER PUBLICATIONS

International Search Report and Written Opinion from IA PCT/US2020/047487 dated Dec. 1, 2020.

(Continued)

*Primary Examiner* — Baisakhi Roy
(74) *Attorney, Agent, or Firm* — Crockett & Crockett, PC; K. David Crockett, Esq.

(57) ABSTRACT

A cannula with a proximally mounted camera and proximally mounted light sources. The lighting sources have beam axes directed distally, toward a workspace at the distal end of the cannula. The light sources are coupled with focusing lenses, to reduce the beam angle of the lighting sources and reduce glare within the cannula tube.

16 Claims, 3 Drawing Sheets

(56) References Cited

U.S. PATENT DOCUMENTS

| | | | |
|---|---|---|---|
| 2009/0234195 A1* | 9/2009 | Chen | A61B 1/0669 |
| | | | 600/249 |
| 2011/0282160 A1* | 11/2011 | Bhadri | A61B 17/3423 |
| | | | 600/236 |
| 2016/0195473 A1* | 7/2016 | Fujiwara | A61B 5/0261 |
| | | | 250/553 |
| 2016/0220324 A1* | 8/2016 | Tesar | G02B 21/0012 |
| 2017/0265734 A1 | 9/2017 | Vayser | |
| 2017/0280988 A1* | 10/2017 | Barbato | A61B 1/317 |
| 2018/0161024 A1* | 6/2018 | Davis | A61B 1/313 |
| 2019/0053699 A1 | 2/2019 | Davis et al. | |

OTHER PUBLICATIONS

Examination Report No. 1 dated Mar. 7, 2022 from Australian Patent Application No. 2020461528.
Examination Report No. 2 dated Jul. 5, 2022 from Australian Patent Application No. 2020461528.
Notice of Submission of Argument dated Jun. 16, 2022 from Korean Patent Application No. 10-2022-7008424.
First Office Action dated Jun. 9, 2022 from Chinese Patent Application No. 202080058092.2.
Notification of Reasons for Refusal dated Aug. 2, 2022 from Japanese Patent Application No. 2022-505621.

* cited by examiner

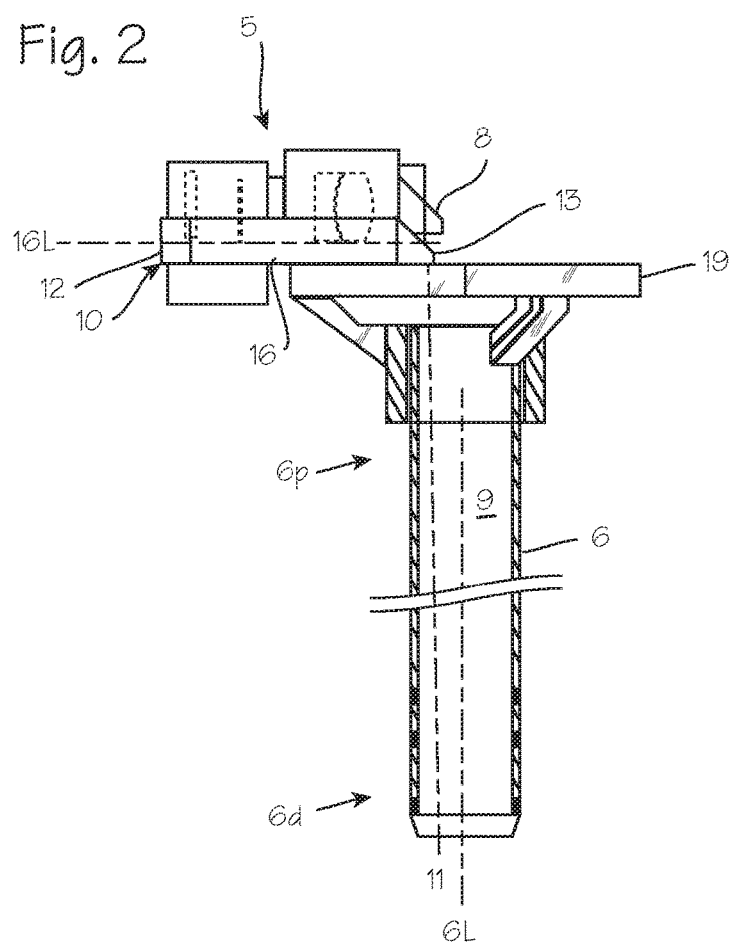
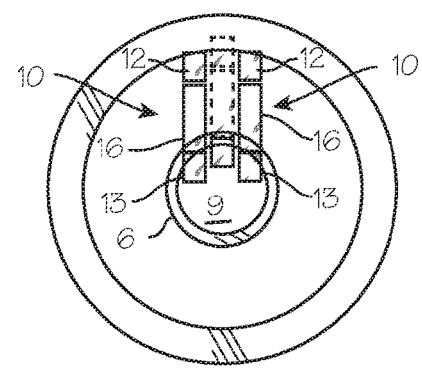
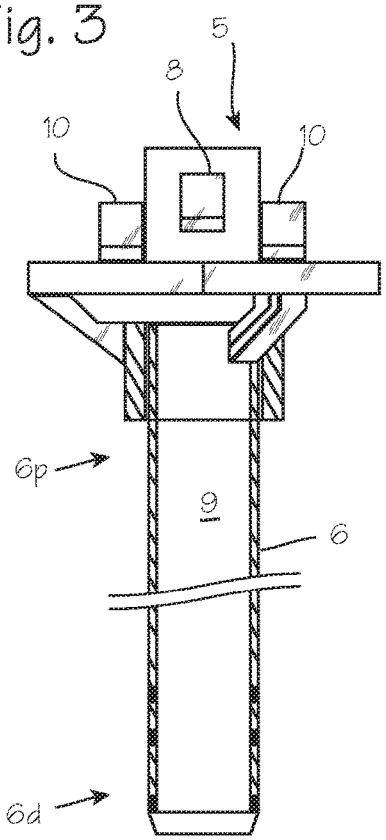
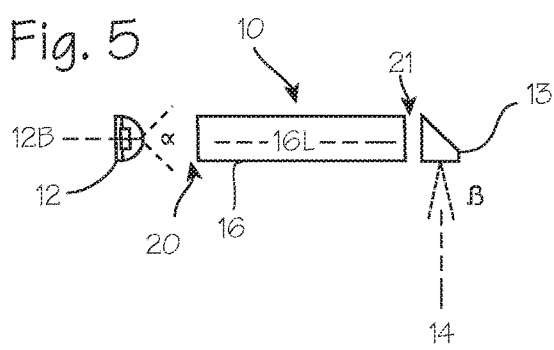

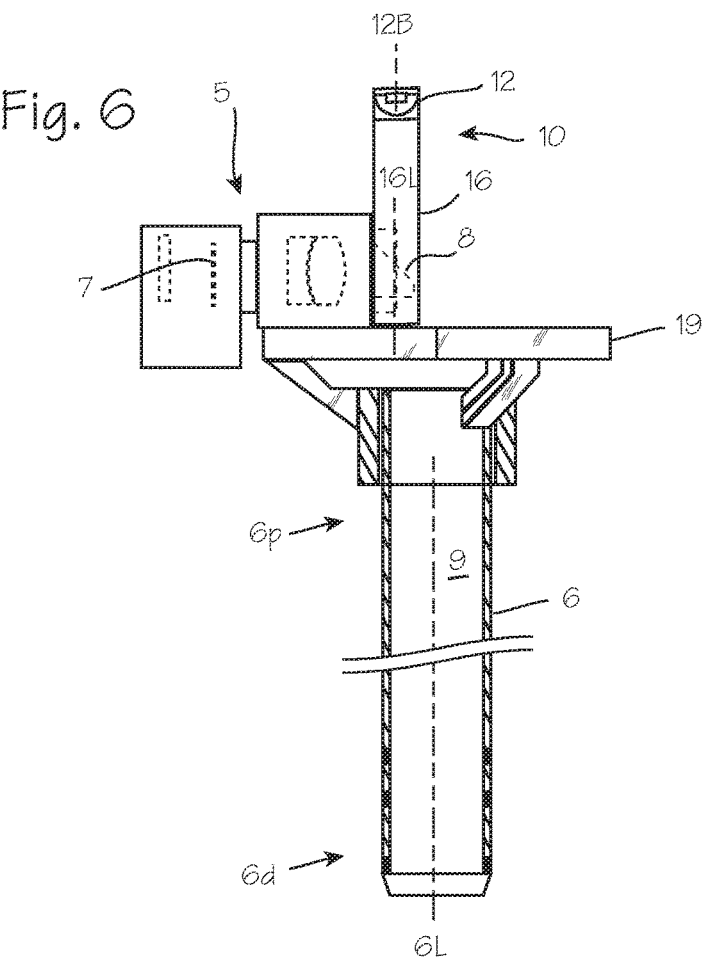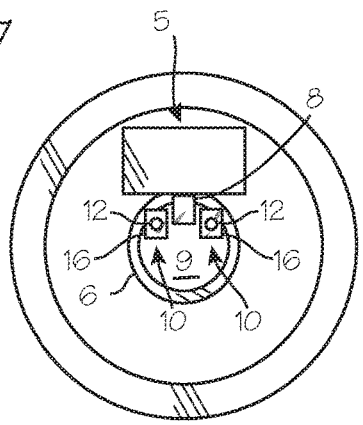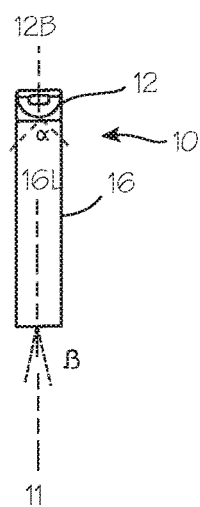

CANNULA WITH ILLUMINATION

FIELD OF THE INVENTIONS

The inventions described below relate to the field of minimally invasive surgery for the treatment of tumors.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury.

Clear visualization and imaging of the blood mass and any surrounding surgical field facilitates removal of the blood mass. In U.S. Pat. No. 10,172,525, we disclose cannula with a camera mounted on the proximal end of the cannula with a view into the cannula lumen and the tissue within and below the lumen. In that system, illumination was provided by LED's mounted at the distal end of the cannula, or through fiber optics extending from the proximal end to the distal end of the cannula.

SUMMARY

The devices and methods described below provide for improved visualization of diseased tissue within the body using a cannula system including a cannula with a proximally mounted camera, with illumination provided by light sources mounted to the proximal end of the cannula. The cannula system includes a cannula tube with a camera assembly mounted on the proximal end of the cannula tube, with a viewing axis directed toward the distal end of the cannula to obtain a view of a surgical workspace near the distal end of the cannula tube. To provide adequate lighting while minimizing glare, the cannula system includes powerful packaged LEDs with a broad beam angle combined with additional lenses to focus output of the LED's to a narrow beam angle. Commercially available packaged LEDs, which comprise a LED, a substrate/chip, and a primary lens, are fitted with secondary optics comprising a narrow focusing lens, to reduce the beam angle of the overall assembly. The secondary optics may comprise a GRIN lens, configured to focus light from the LED to a narrow beam angle for transmission through the cannula to the workspace at the distal end of the cannula. For example, for a 13 cm long cannula with a 9 mm inner diameter, the lens may be configured to provide an output beam angle of about 3.5°.

BRIEF DESCRIPTION OF THE DRAWINGS

FIGS. 2, 3 and 4 illustrate a cannula system with LED's and focusing lenses configured to narrow the beam angle of the light transmitted into the cannula tube.

FIG. 5 shows details of the lighting assembly shown if FIGS. 1, 2 and 3.

FIGS. 6, 7 and 8 illustrate a lighting assembly without a prism, in which the optical axis is aligned with the length of the cannula tube.

DETAILED DESCRIPTION OF THE INVENTIONS

Figure 1:
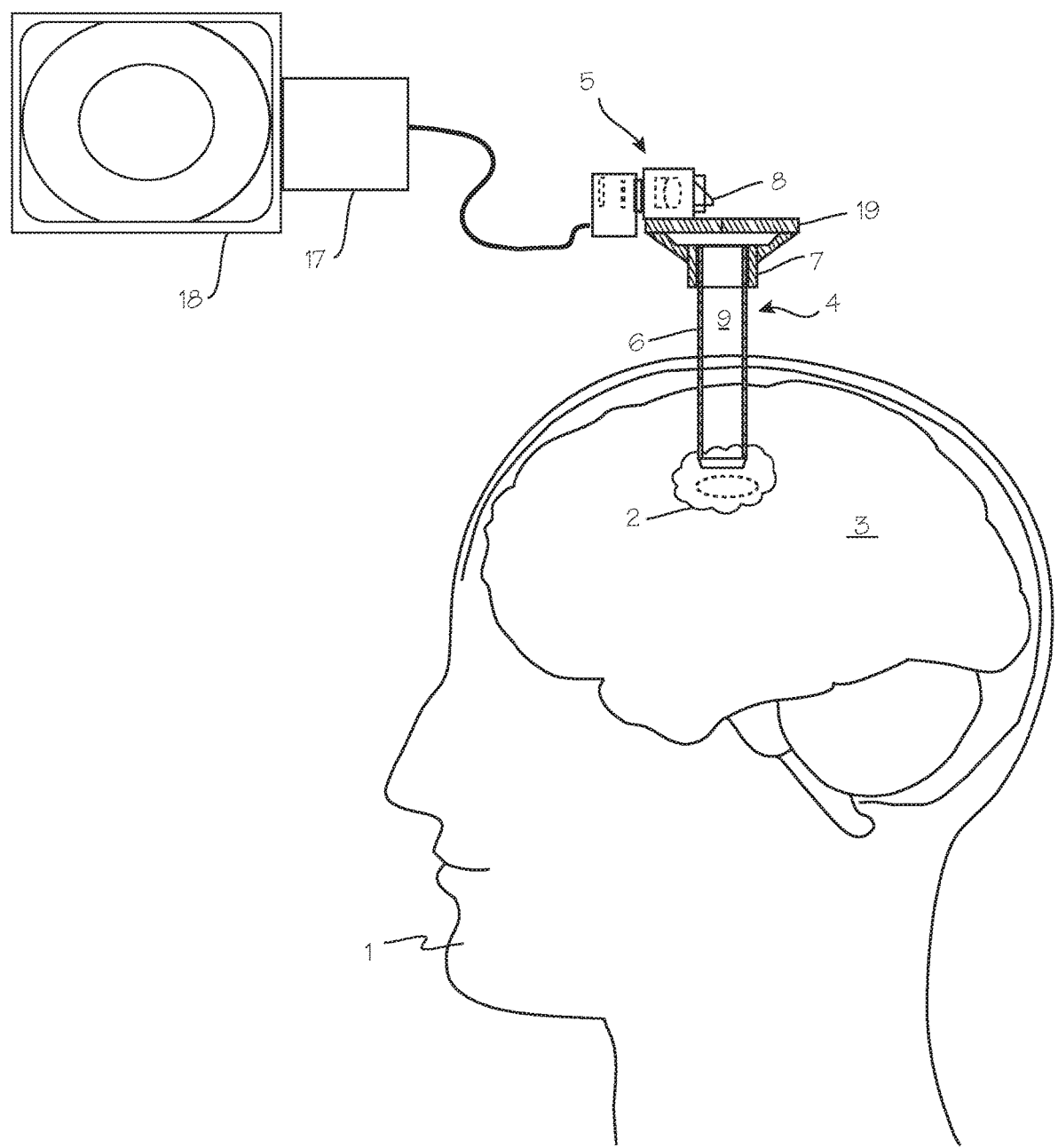
FIG. 1 illustrates a patient with a blood mass in the brain that necessitates surgical intervention, with a cannula which has been inserted into the brain, with the distal end of the cannula proximate the blood mass.

FIGS. 1, 2 and 3 illustrate a cannula system that may be conveniently used in a minimally invasive surgery. FIG. 1 illustrates a patient 1 with diseased tissue 2 in the brain 3 that necessitates surgical intervention, with a cannula 4 which has been inserted into diseased tissue, with the distal end of the cannula proximate the diseased tissue. The diseased tissue may be a glioma or glioblastoma in the brain, an ependymoma in the spine, or other diseased tissue.

A camera 5 is mounted on the proximal rim of the cannula, with a portion of the camera overhanging the rim of the cannula and disposed over the lumen of the cannula, and is operable to obtain video or still images of the distal end of the cannula lumen, including target tissue at the distal end of the cannula such as the brain and any diseased tissue in the brain. As shown in both FIGS. 1 and 2 and 3, the cannula comprises a cannula tube 6 with a distal end 6d adapted for insertion into the body of the patient. The camera assembly 5 is secured to the proximal end 6p of the cannula. The camera assembly includes an imaging sensor 7 and a prism, reflector or other mirror structure or optical element 8, overhanging the lumen 9 of the cannula tube. Preferably, for use in the brain, a portion of the camera assembly, such as the prism, reflector or mirror, extends into the cylindrical space defined by the lumen of the cannula tube and extending proximally beyond the proximal end of the cannula, and is spaced from the proximal end of the cannula, and extends only slightly into the cylindrical space. The distal-most optical surface of the camera assembly, whether it be the distal face of the prism 8 or an objective lens with a viewing axis directed toward the distal end of the cannula, used without a prism, is located at the proximal end of the cannula tube, and preferably disposed proximally of the proximal end of the cannula tube.

As shown in FIGS. 2 and 3, the cannula also includes one or more lighting assemblies 10 with an output beam axis 11 The lighting assemblies include light sources 12 and associated optics, if any, which in the illustrated include prisms 13 having an output axis 14 (which in this embodiment is coincident with the output beam axis 11 of the lighting assembly), and lenses 16, which may be used in this configuration to direct light from the light sources into the lumen, aimed at the workspace at the distal end of the cannula tube and toward target tissue. FIG. 1 also shows the control system 17, which is configured and operable to operate the light sources, obtain video image data captured by the camera, and generate/translate corresponding video image data for display on the display screen 18. The camera assembly and lighting assemblies may be supported and held proximally to the proximal end of the cannula tube on a mounting structure 19, which in this embodiment comprises a ring of larger diameter than the cannula tube, fixed above the proximal end of the cannula tube.

FIGS. 2, 3, 4, and 5 illustrate the construction of the lighting assemblies 10. These lighting assemblies include the light source 12, prism 13 and the lens 16 positioned between the light source and the prism. The light source is characterized by a beam axis 12B, and a broad beam angle α, which may be the result of a un-lensed LED, or a packaged LED with a lens configured to focus light from the LED into the broad beam angle. The packaged LED is typically provided in a form that comprises a substrate, the light-emitting diode itself, and a lens covering the light-emitting diode. In the case of a white light LED, the packaged LED may also comprise a phosphor (to convert some blue light from the diode into red and green light, to produce a package that emits white light). A typical beam angle for a packaged LED may be in the range of 30° to 180°. When used in the cannula system of FIGS. 1 through 4, this wide beam angle would result in excessive glare which obscures images obtained with the camera assembly. To reduce this glare, the lens 15 is a focusing lens provided in the form of a convex lens or a gradient index lens (a GRIN lens) or a collimator lens, which functions to focus light from the packaged LED into a narrower beam angle. A suitable combination of packaged LED and lens is (1) a CREE® XQEAWT led and (2) an Edmunds #64-520 GRIN lens available from Edmunds Optics. A GRIN lens is preferred due to its small cross-section (the cross-section perpendicular to its optical axis) for a given focusing power, which facilitates placement of the lighting assembly on the proximal end of the cannula tube. The prism is preferably a right angle prism, but different forms of prism may be used, to accommodate different angles between the optical axis (the long axis, in this example) 16L of the GRIN lens, output beam axis 11 and the central axis 6L of the cannula tube. The overall lighting assembly has an output beam axis which corresponds to a viewing axis of the prism and the output beam axis 11 is at an angle to the optical axis 16L of the focus lens (in the example shown in FIGS. 2, 3, 4). In the case of a right angle prism, the optical axis of the focusing lens may be perpendicular to the viewing axis of the prism. The distal-most optical surface of the lighting assembly, whether it be the distal face of the prism 13 or a distal surface of the focusing lens (where the focusing lens optical axis is directed toward the distal end of the cannula, used without a prism, as shown in FIGS. 6 and 7) is located at the proximal end of the cannula tube, and preferably disposed proximally of the proximal end of the cannula tube.

The lighting assembly may be configured with an air gap 20 between the packaged LED and the lens and an air 21 gap between the lens and the prism. With this combination using a CREE® XQEAWT led and an Edmunds #64-520 GRIN lens the resultant beam angle β, centered on the lighting assembly beam axis 10B, is about 3.5°.

FIGS. 6 and 7 illustrate a lighting assembly without a prism, in which the optical axis (of the focusing lens) 16L is aligned with the length of the cannula tube 6. Other features of this embodiment are similar to the features of FIGS. 2 through 4, including the cannula 4 and the cannula tube 6, the camera assembly 5 and the prism 8. The LED's are disposed with a beam axis 12B directed distally into the cannula lumen and toward the distal end of the cannula tube, with the lens 16 aligned with its optical axis 16L aligned with the LED beam axis and also pointed distally, toward the cannula lumen and the distal end of the cannula tube. In the configuration, the prism is not necessary. The overall lighting assembly in this embodiment has an output beam axis which corresponds to the optical axis of the focus lens, and this output beam axis is directed toward the distal end of the cannula tube.

In the top view of FIG. 7, the positions of the light sources, and the corresponding lenses 16 and LED light sources 12, along with the camera assembly 5 and the camera prism 8, are shown, with the light sources and camera prism overhanging the lumen 9 of the cannula tube 6 to a limited extent, allowing for illumination and visualization of the workspace at the distal end of the cannula tube while also allowing for passage of tools into the workspace, through the cannula tube. FIG. 8 shows the relationship between the lighting assembly 10 with the light source 12 and its beam angle α transmitting light into a GRIN lens 16, with the light leaving the GRIN lens with a narrow beam angle β along the lighting assembly beam axis 11.

The output beam angle may be slightly larger or smaller, depending on the dimensions of the cannula. For a relatively short, wide cannula 7 cm long with a 16 mm inner diameter, for example, a narrow beam angle of about 10 to 15°, more preferably about 13°, will provide good illumination with reduced glare. For a 14 cm long cannula with a 9 mm inner diameter, a narrow beam angle of about 3 to 5°, more preferably about 3.7°, will provide good illumination with reduced glare. More generally, a configuration of light source and focusing lens providing an output beam angle of less than about 20° may be used to provide good illumination with minimal glare.

The illustrations show a beam axis (the center of light leaving the lens) of the GRIN lens coincident with the optical axis of the GRIN lens, the beam axis may be altered by positioning the LED off-center relative to the longitudinal center of the GRIN lens (which typically is the optical axis). This will cause the output beam axis of the GRIN lens in Figured 6 and 7 to depart from parallel to the optical axis. Thus, placement of the LED, such that the beam axis of the LED is displaced from the optical axis of the GRIN lens will cause the output beam axis of the GRIN lens to be at an axis to the optical axis. The output beam axis may thus be aimed at the center of the distal opening of the cannula, to intersect a central axis (or other feature) of the cannula tube, while the lighting assembly output remains near the circumference of the cannula tube.

The configurations the lighting assemblies and cannula result in minimal intrusion of the distal-most optical surface of the lighting assembly into the cannula lumen, or the space over the lumen, so that a surgeon may pass surgical tools through the cannula while the lighting assemblies are disposed on the proximal end of the cannula tube to illuminate the surgical field at the distal end of the cannula, and while the camera also has a distal-most optical surface disposed with minimal intrusion into the cannula lumen, or the space over the lumen, so that a surgeon may pass surgical tools through the cannula while the camera is disposed over the proximal end of the cannula. The benefits of the lighting assemblies which provide narrow output beam allow for a camera and one or more lighting assemblies to be provided at the end of a cannula and still allow passage of surgical tubes into the cannula, the cannula system can be configured with one or more lighting assemblies without a camera disposed on the proximal end of the camera, to provide lighting with minimal glare in a cannula to be used with a camera or microscope provided elsewhere.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A cannula system for accessing a surgical field, said cannula system comprising:

a cannula comprising a cannula tube (6) with a proximal end and a distal end and a lumen (9) extending from the proximal end to the distal end; and a lighting assembly (10) secured to the proximal end of the cannula tube;

wherein the lumen and lighting assembly are configured to allow passage of surgical tools through the cannula while the lighting assembly is disposed on the proximal end of the cannula tube;

said lighting assembly comprising a light source (12) and a focusing lens (16), said light source having a first beam axis and a first beam angle ($\alpha$), said first beam axis aligned with an optical axis (11) of said focusing lens (16), said lighting assembly (10) having an output beam angle ($\beta$) and an output beam axis, wherein said output beam axis is directed toward the distal end of the cannula tube, wherein said output beam angle ($\beta$) is smaller than said first beam angle ($\alpha$);

whereby the lighting assembly provides adequate illumination for the surgical field with reduced glare within the cannula tube.

2. The cannula system of claim 1, wherein:

a camera assembly (5) secured to the proximal end of the cannula tube, with a portion of the camera assembly overhanging the lumen and extending into the lumen or a cylindrical space defined by the lumen of the cannula tube and extending therefrom.

3. The cannula system of claim 2, wherein:

the camera assembly has a distal-most optical surface which is disposed at the proximal end of the cannula tube.

4. The cannula system of claim 2, wherein:

the camera assembly has a distal-most optical surface which is disposed at the proximal end of the cannula tube; and the lighting assembly has a distal-most optical surface which is disposed at the proximal end of the cannula tube.

5. The cannula system of claim 2, wherein:

the camera assembly has a distal-most optical surface which is disposed proximal to the proximal end of the cannula tube.

6. The cannula system of claim 2, wherein:

the camera assembly has a distal-most optical surface which is disposed proximal to the proximal end of the cannula tube; and the lighting assembly has a distal-most optical surface which is disposed proximal to the proximal end of the cannula tube.

7. The cannula system of claim 1, wherein:

the lighting assembly further comprises a prism (13) disposed on a side of the focusing lens opposite the light source, with the optical axis of the focusing lens aligned with the prism, wherein the output beam axis corresponds to a viewing axis of the prism and the output beam axis is at an angle to the optical axis of the focus lens.

8. The cannula system of claim 1, wherein:

the lighting assembly has an output beam axis which corresponds to the optical axis of the focusing lens, and the output beam axis is directed toward the distal end of the cannula tube.

9. The cannula system of claim 1, wherein:

the lighting assembly has a distal-most optical surface which is disposed at the proximal end of the cannula tube.

10. The cannula system of claim 1, wherein:

the lighting assembly has a distal-most optical surface which is disposed proximal to the proximal end of the cannula tube.

11. The cannula system of claim 1, wherein:

the focusing lens is a GRIN lens.

12. The cannula system of claim 1, wherein:

the focusing lens is a convex lens.

13. The cannula system of claim 1, wherein:

the lighting assembly further comprises a prism (13), arranged such that the optical axis of the focusing lens intersects the prism, and the prism reflects light from the focusing lens into the lumen of the cannula tube.

14. The cannula system of claim 1, wherein:

the lighting assembly further comprises a prism (13), and the optical axis of the focusing lens is perpendicular to a long axis of the cannula tube, and the prism reflects light from the focusing lens into the lumen.

15. The cannula system of claim 1, wherein:

the output beam angle is 20° or less.

16. The cannula system of claim 1, wherein:

the output beam angle is 5° or less.

\* \* \* \* \*